US012708271B2

(12) United States Patent
Bidlack

(10) Patent No.: US 12,708,271 B2
(45) Date of Patent: Aug. 18, 2026

(54) METHOD AND SYSTEM FOR DETECTING MOLAR INCISOR HYPOMINERALIZATION USING HIGH RESOLUTION RAMAN ANALYSES OF TOOTH COMPOSITION

(71) Applicant: ADA FORSYTH INSTITUTE, INC., Somerville, MA (US)

(72) Inventor: Felicitas B. Bidlack, Somerville, MA (US)

(73) Assignee: ADA FORSYTH INSTITUTE, INC., Somerville, MA (US)

( * ) Notice: Subject to any disclaimer, the term of this patent is extended or adjusted under 35 U.S.C. 154(b) by 65 days.

(21) Appl. No.: 17/452,053

(22) Filed: Oct. 22, 2021

(65) Prior Publication Data

US 2022/0125316 A1 Apr. 28, 2022

Related U.S. Application Data

(60) Provisional application No. 63/104,486, filed on Oct. 22, 2020.

(51) Int. Cl.
*A61B 5/00* (2006.01)

(52) U.S. Cl.
CPC .......... *A61B 5/0088* (2013.01); *A61B 5/0066* (2013.01); *A61B 5/742* (2013.01)

(58) Field of Classification Search
CPC ....... A61B 5/0088; A61B 5/0075; A61B 6/14; A61B 5/0066; A61B 5/742; G01N 21/65; G01J 3/44
See application file for complete search history.

(56) References Cited

U.S. PATENT DOCUMENTS

| | | | |
|---|---|---|---|
| 7,796,243 | B2 | 9/2010 | Choo-Smith et al. |
| 10,238,291 | B2 | 3/2019 | González Fernández et al. |

(Continued)

FOREIGN PATENT DOCUMENTS

| | | |
|---|---|---|
| JP | 2018521701 A | 8/2018 |
| RO | 2013 00043 U1 | 10/2015 |

(Continued)

OTHER PUBLICATIONS

Taube [Deviations Of Inorganic And Organic Carbon Content In Hypomineralised Enamel, Journal Of Dentistry 43, 2015, 269-278] (Year: 2015).*

(Continued)

*Primary Examiner* — Oommen Jacob

(74) *Attorney, Agent, or Firm* — Hamilton, Brook, Smith & Reynolds, P.C.

(57) ABSTRACT

A system and method provides in vivo identification of hypomineralization and distinction between enamel defects. Chemical composition measurements of enamel on a target surface of a tooth are obtained using a Raman spectroscope. A system creates an evaluation profile of the target surface by evaluating the Raman intensity associated values with both inorganic and organic components. A composite metric is calculated for the evaluation profile based on the values associated with the organic and inorganic components of the evaluation profile. The system can then identify hypomineralization and a type of enamel defect through proximity of the composite metric of the evaluation profile to a composite metric associated with known hypomineralization. If hypomineralization is identified, notice is provided to a user.

12 Claims, 15 Drawing Sheets
(13 of 15 Drawing Sheet(s) Filed in Color)

(56) References Cited

U.S. PATENT DOCUMENTS

| | | | | |
|---|---|---|---|---|
| 2005/0147600 | A1 | 7/2005 | Acton et al. | |
| 2005/0283058 | A1* | 12/2005 | Choo-Smith | A61B 5/0088 356/73 |
| 2010/0279248 | A1* | 11/2010 | Mourad | A61B 5/7275 433/29 |
| 2013/0071953 | A1 | 3/2013 | Hess et al. | |
| 2018/0242957 | A1 | 8/2018 | Tariyal et al. | |
| 2018/0263498 | A1 | 9/2018 | Iftimia et al. | |
| 2018/0348235 | A1 | 12/2018 | Vigué et al. | |
| 2019/0242894 | A1 | 8/2019 | Oved et al. | |
| 2019/0369025 | A1* | 12/2019 | Yang | A61B 5/4547 |
| 2023/0184786 | A1 | 6/2023 | Hardt et al. | |

FOREIGN PATENT DOCUMENTS

| | | | |
|---|---|---|---|
| WO | 2006/039819 | A1 | 4/2006 |
| WO | 2021/189015 | A1 | 9/2021 |

OTHER PUBLICATIONS

Solis [Early Detection Of Dental Fluorosis Using Raman Spectroscopy And Principal Component Analysis, Lasers Med Sci (2015) 30:1675-1681] (Year: 2015).*

Crombie [Surface Integrity Governs the Proteome of Hypomineralized Enamel, Journal of Dental Research vol. 89, Issue 10, Oct. 2010, pp. 1160-1165]. (Year: 2010).*

Ravikumar [Applications of Raman Spectroscopy in Dentistry: Analysis of Tooth Structure, Applied Spectroscopy Reviews, 50:332-350, 2015], (Year: 2015).*

Coello [Quantitative Evaluation Of The Mineralization Level Of Dental Tissues By Raman Spectroscopy, Biomed. Phys. Eng. Express 1 (2015) 045204], (Year: 2015).*

Bekes, et al., "Diagnosis, Classifications and Treatment Stategies of MIH-Affected Teeth," *Molar Incisor Hypomineralization,* pp. 47-58, Jan. 3, 2020.

Fraser, ct al., "A Raman Spectroscopic Study of Teeth with Molar-Incisor Hypomineralisation," *Journal of Raman Spectroscopy,* 46(2), Jan. 16, 2015.

González-Solís, et al., "Early Detection of Dental Fluorosis Using Raman Spectroscopy and Principal Component Analysis," *Lasers Med Sci.,* (6):1675-81 (Aug. 14, 2014).

Hubbard, et al., "Molar Hypomineralisation: A Call to Arms for Enamel Researchers," *Front. Physiol.* 2017, 8, 546.

Jain, et al., "Misdiagnosis: How Uncommonly Common Is It?" *J. Clin. Diagn. Res.* 2018.

Krämer, et al., "Bonding Strategies for MIH-Affected Enamel and Dentin," *Dent. Mater. Off. Publ. Acad. Dent. Mater.* 2018, 34 (2), 331-340.

Malmberg, et al., "Molecular Insights into Hypomineralized Enamel," *Eur. J. Oral Sci.* 2019, 127 (4), 340-346.

Notification of Transmittal of the International Search Report and the Written Opinion of the International Searching Authority, or the Declaration, issued for International Application No. PCT/US2021/072004, entitled "Method and System for Detecting Molar Incisor Hypomineralization Using High Resolution Raman Analyses of Tooth Composition," mailed on Jan. 27, 2022.

Silva, et al., "Knowledge and Attitudes Regarding Molar Incisor Hypomineralisation amongst Saudi Arabian Dental Practitioners and Dental Students," *Eur. Arch. Paediatr. Dent. Off. J. Eur. Acad. Paediatr. Dent.* 2016, 17 (4), 215-222.

Weerheijm, et al., "Judgement Criteria for Molar Incisor Hypomineralisation (MIH) in Epidemiologic Studies: A Summary of the European Meeting on MIH Held in Athens," 2003. *Eur. J. Paediatr. Dent.* 2003, 4 (3), 110-113.

Williams, et al., "Pathogenesis of Molar Hypomineralisation: Hypomineralised 6-Year Molars Contain Traces of Fetal Serum Albumin," *Front. Physiol.* 2020, 11, 619.

Plasma Renin Activity (PRA) ELISA, Immuno-Biological Laboratories, Inc, Oct. 17, 2022, Retrieved from https://www.ibl-america.com/content/elisa/IB59131.pdf, pp. 3.

"International Preliminary Report on Patentability," issued for International Application No. PCT/US2021/023348, entitled "Methods of Detecting and Treating Immune Responses Associated with Viral Infection," date of Issuance: Sep. 20, 2022.

"International Preliminary Report on Patentability," issued for International Application No. PCT/US2021/072004, entitled "Methods of Detecting and Treating Immune Responses Associated with Viral Infection," dated of Issuance: Apr. 13, 2023.

International Search Report and Written Opinion received for PCT Patent Application No. PCT/US21/023348, mailed on Jul. 12, 2021, 14 pages.

Crombie et al., "Characterisation of developmentally hypomineralised human enamel", Journal of Dentistry, vol. 41, No. 7, Jul. 2013, pp. 611-618.

Weerheijm, K.L., "Molar Incisor Hypomineralization (MIH): Clinical Presentation, Aetiology and Management", Paedodontology, vol. 31, No. 1, Jan. 2004, pp. 9-12.

* cited by examiner

1400

METHOD AND SYSTEM FOR DETECTING MOLAR INCISOR HYPOMINERALIZATION USING HIGH RESOLUTION RAMAN ANALYSES OF TOOTH COMPOSITION

RELATED APPLICATION

This application claims the benefit of U.S. Provisional Application No. 63/104,486, filed on Oct. 22, 2020. The entire teachings of the above application are incorporated herein by reference.

BACKGROUND

Minerals compose 96% by weight of tooth enamel. The primary mineral constituent is biological hydroxyapatite. Diseases and developmental dental defects (D3) can cause changes in the mineral content of enamel. Two common enamel D3 disorders are fluorosis and molar hypomineralization (MH) (or molar-incisor hypomineralization (MIH)), also known commonly as "chalky teeth."

Fluorosis is a dental defect characterized by hypomineralized tooth enamel. This hypomineralization is caused by ingestion of excessive fluoride during enamel formation. It often manifests as a discoloration of the tooth and sometimes as physical damage to the teeth. Most dental fluorosis appears as white spots on the tooth surface that may be barely noticeable and do not affect dental function.

MH is a developmental dental defect that prevents enamel from forming properly. MH causes the tooth enamel to be softer and therefore it can trigger a variety of problems such as increased sensitivity, toothaches and accelerated tooth decay and attrition. An estimated 1 in 5 school children have MH, corresponding to an estimated 14 million new cases each year. It can affect primary dentition and permanent dentition, often the permanent molars. Patients experience high pain sensitivity, and the affected enamel is characterized by demarcated opacity and elevated protein content including albumin that prevents the completion of crystal growth during the formation process. As a result, the enamel is soft, hypomineralized, prone to posteruptive decay, breakdown, and loss.

Raman spectroscopy is a photonic analytical technique that typically works by focusing a laser beam onto the tissue of interest. The light is re-emitted by the tissue, also referred to as Raman-scattering or Raman effect, provides data information about the molecular vibrations by measuring the differences between the energy of the incident photons and that of the scattered photons. Raman microscopy measures the scattering of the light which enables users to obtain a compositional and structural fingerprint of mineralized tissues. Raman spectroscopy has been used as a research tool to detect changes in the composition of tooth enamel. These changes can in turn serve as an indication of a change in health status.

Current research applications of Raman spectroscopy in dentistry focus on the early detection of caries and periodontal disease, and identification of microbial flora. For example, U.S. Pat. No. 10,238,291, "Method for Diagnosing Dental Demineralization Processes" issued Mar. 26, 2019, describes the use of Raman spectroscopy for the ex vivo diagnosis of dental demineralization. As noted in U.S. Pat. No. 10,238,291, clinical studies in hard mineralized tissue continue to be few.

SUMMARY

MH can be difficult for the clinician to identify and is frequently misdiagnosed as fluorosis, caries, or masked by caries in the MH affected tooth area. A 2018 study found that 67% of general dentists were unable to correctly diagnose MH. A lack of education in dental training, a lack of guidance in diagnosis, and lack of correct diagnosis and correct treatment are pervasive global problems in addressing and alleviating the disease recognition and burden. As a result of its high prevalence and diagnostic difficulty, MH is a significant public health burden. Making an accurate and early diagnosis of MH is important so that appropriate approaches to managing the affliction can be implemented. There is a clinical need for easily distinguishing MH from other hypomineralizing effects such as fluorosis. To date there is no such test available.

The invention provides a diagnostic aid for the specific distinction between fluorosis and identification of the developmental dental defect of molar hypomineralization (Chalky teeth) which affects the primary and/or permanent molars of 1 in 5 children globally (https://www.thed3group.org/media.html). MH affected enamel is soft due to fetal serum albumin that prevents completion of enamel mineralization and is retained in the erupted tooth enamel. As a result, MH teeth are prone to caries, abrasion and fracture requiring surface coverage with fillings or replacement of the entire crown or tooth extraction. Poor bonding of fillings and orthodontic needs after tooth extractions require repeated dental treatments, often performed under general anesthesia. While fluoride aids in surface hardening, its effectiveness is limited because enamel crystals remain embedded in soft organics.

In some aspects, the methods and systems described herein relate to the in vivo identification of hypomineralization and distinction between enamel defects. Embodiments of the method include obtaining chemical composition measurements of enamel on a target surface of a tooth using a Raman spectroscope. Raman spectroscopy can be non-invasive and a non-destructive analytical method to characterize mineralized tissues and enamel, and can discern between healthy and defective tooth enamel.

A system creates an evaluation profile of the target surface by evaluating the Raman intensity values associated with inorganic components of PO4 with peak positions at 430 cm-1, 577 cm-1, 960 cm-1, and CO3 at 1070 cm-1, and organic components C—H at 1440 cm-1, SH at 2590 cm-1 and C—H at 2950 cm-1. A composite metric is calculated for the evaluation profile based on the values associated with the organic and inorganic components of the evaluation profile. The system can then identify hypomineralization and a type of enamel defect through proximity of the composite metric of the evaluation profile to a composite metric associated with known hypomineralization. If hypomineralization is identified, notice is provided to a user. In some embodiments, the system may provide the user with the type of enamel defect identified.

In embodiments, the system may use the evaluation profile to identify hypomineralization and a type of enamel defect through proximity of the evaluation profile to a hypomineralization profile characterized by differences in absence/presence of peaks that are characteristic of healthy tooth enamel, and differences in the position and shape of peaks in hypomineralized enamel, specifically for PO4 (430 cm-1), PO4 (577 cm-1), PO4 (960 cm-1), and CO3 (1070 cm-1), C—H (1440 cm-1), SH (2590 cm-1) and C—H (2950 cm-1). If hypomineralization is identified, notice is provided to a user. In some embodiments, the system may provide the user with the type of enamel defect identified.

A Raman spectrum provides specific information on chemical structure, mineral phase, and degree of crystallinity. Each peak in the spectrum represents the vibrational properties of the respective chemical entity (i.e. phosphate from hydroxyapatite, C—H bonds or C═O double bounds from organic molecules like proteins). Properties of these peaks can be quantified using various parameters like their intensity, peak width, area under the curve and peak position.

In some aspects, the system identifies the type of enamel defect by distinguishing fluorosis and molar hypomineralization as characterized by demarcated opacity, molar incisor hypomineralization, incisor hypomineralization, deciduous molar hypomineralization, and hypomineralized second primary molars.

In some aspects, in addition to Raman spectroscopy measurements, the system may include a handheld optical coherence tomography (OCT) device, or functional components of an OCT to obtain the material density of a target area of a tooth. The system may obtain material density measurements of enamel on the surface of the tooth, including enamel thickness towards underlying dentin. When creating an evaluation profile, the system may evaluate an extension of an enamel defect from the tooth surface through the enamel thickness towards the underlying dentin. A marked increase in reflectivity to healthy enamel may further provide an indication of the type of enamel defect. In yet additional embodiments, the material density and the chemical composition measurements are obtained with a non-invasive fiber optic sensor The measurements from the device can be used to distinguish between enamel defects in vivo. Specifically, differences in the underlying etiologies are used to distinguish between MH and fluorosis.

In other aspects, the system obtain an image of the tooth and generate an adjusted image of the tooth highlighting an intensity value of the composite metric of the evaluation profile obtained at a particular portion of the tooth. The system may then display the adjusted image highlighting the intensity value of the composite metric.

The technology described herein provides a new method for accurately diagnosing MIH that significantly reduces the rate of misdiagnosing the condition as fluorosis.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments.

DETAILED DESCRIPTION

Figure 1B:
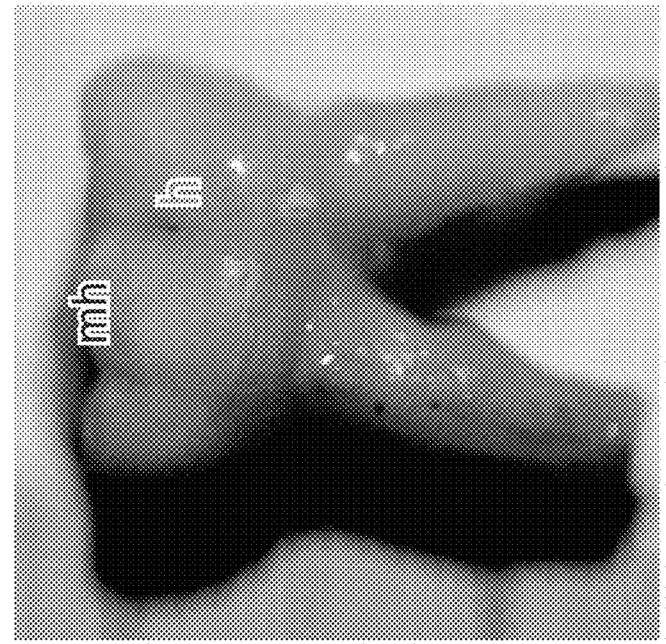
FIG. 1B is a primary molar showing differences in the Raman spectroscopy signature from regions of healthy enamel and defective enamel.

A description of example embodiments follows.

To date, the reliable diagnosis of MH is not standard of care and 67% of cases are misdiagnosed, mostly as fluorosis. There is an absence of existing tools applicable in clinical settings to reliably distinguish between enamel defects at the time of tooth eruption and in erupted teeth. The defective enamel in MH is characterized by smaller enamel crystals and incomplete mineralization due to the retention of albumin during tooth formation. The albumin content and mineral composition define the unique properties of MH enamel, discern it from other enamel defects, and result in treatment that is targeted on MH specific requirements for lasting treatment success, which are different from both fluorosis and caries. Based on the unique MH characteristic enamel properties, it is possible to distinguish it from different dental defects, which allows dentists to make a correct diagnosis. Dentists will then be able to correctly and early diagnose, develop treatment plans, and provide appropriate treatments for their patients, thereby reducing the societal burden of undiagnosed MH.

Raman spectroscopy is a non-invasive technique that allows for the biochemical characterization of tissues. It typically works by focusing a laser beam onto the tissue of interest. The light is re-emitted by the tissue as Raman scattering. Confocal Raman microscopy measures changes in energy and direction of the emitted light which enables users to analyze the composition and structural features of mineralized tissues. Raman spectroscopy has been used as a research tool to detect changes in the composition of enamel. These changes can in turn serve as an indication of a change in health status. A Raman spectrum provides specific information on chemical structure, mineral phase, and degree of crystallinity. Each peak in the spectrum represents the vibrational properties of the respective chemical entity (i.e. phosphate from hydroxyapatite, C—H bonds or C═O double bounds from organic molecules like proteins. Properties of these peaks can be quantified using various parameters like their intensity, peak width, area under the curve and peak position.

| Peak Position | Raman Shift ($cm^{-1}$) | |
|---|---|---|
| $PO_4$ | 430 | Properties of the mineral phase and crystallinity |
| $PO_4$ | 577 | |
| $PO_4$ | 960 | |
| $CO_3$ | 1070 | |
| C—H | 1440 | Properties of organic component of tooth enamel |
| Amide I | 1660 | |
| SH | 2590 | |
| C—H | 2950 | |

Current research applications of Raman spectroscopy in dentistry focus on the early detection of caries and periodontal disease, and identification of microbial flora. However, current methods described in the literature involve ex vivo analysis of enamel samples. The application of Raman for ex vivo analyses of tooth enamel requires the use of extracted teeth and precludes the usefulness to preserve or dental health or apply the appropriate and most efficient treatment to tooth enamel affected by hypomineralization. A handheld probe is required to perform the analysis as a non-invasive diagnostic tool in vivo, thus avoiding the need for destructive or invasive procedures to take a biopsy. The ex vivo application is not helpful to determine treatment needs in the clinic. The in vivo diagnosis allows for early assessment of tooth enamel, even at the time of tooth emergence.

The invention describes a method for utilizing in vivo measurements obtained from a handheld Raman spectroscopy system, and in some embodiments combined Raman spectroscopy and OCT system, for providing a discriminatory diagnosis of MIH versus fluorosis. In the dental setting, existing devices that use OCT and Raman spectroscopy are invasive in that they are typically designed for sampling interstitial tissues by inserting a needle into a sample and positioning an optical probe to take measurements to evaluate soft tissues or for identifying fissures or caries lesions between teeth. One such example is described in U.S. Pat. No. 11,109,759, "Apparatus and Method for Assessment of Interstitial Tissue" issued Sep. 7, 2021. Embodiments consistent with the present invention use a flat non-invasive fiber optic contact for obtaining surface measurements on the tooth.

A comparison of the specific enamel effects of MEI and fluorosis allows for the reliable discernment of one condition versus the other. This is due to the underlying etiologies of both conditions, which create differences in the affected enamel regions. These differences include the chemical composition, mineral density, structural organization, porosity, hardness, brittleness, mineral crystal size, mineral lattice defects, proteomes, and peptidomes.

Using Raman and OCT data, or even Raman data alone, embodiments may identify hypomineralization and type of enamel defect by discerning fluorosis from MIH in tooth enamel.

Figure 1A:
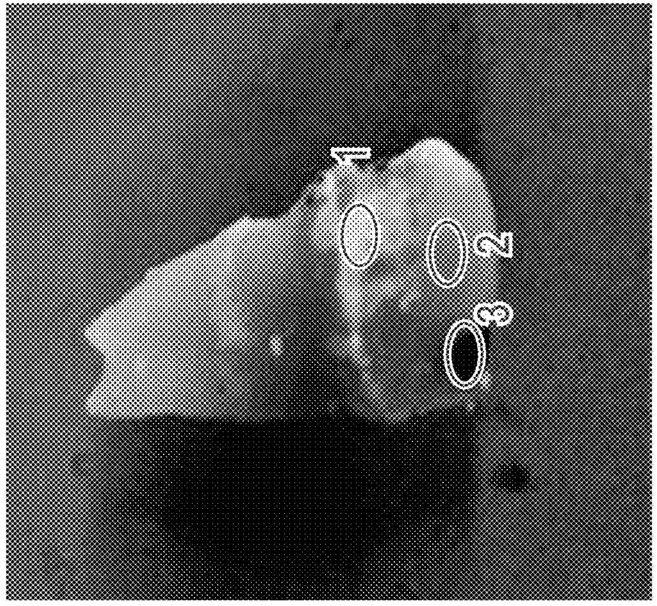
FIG. 1A is an incisor showing differences in the Raman spectroscopy signature from regions of healthy enamel and defective enamel.

FIG. 1A illustrates an example incisor, FIG. 1B, FIG. 2A, FIG. 2B and FIG. 2C are molars that presented differences in the Raman spectroscopy signature at different regions of the enamel surface, illustrating distinctions between regions of healthy enamel and defective enamel.

With respect to FIG. 1A, Raman spectra were obtained from different areas of the tooth crown. Section 1 is affected by fluorosis, where in contrast, Section 2 is healthy enamel. Section 3 is a caries lesion. The table below summarizes the results of Raman spectroscopy on sections 1 and 2 of FIG. 1A.

| | HEALTHY | | | | FLUORITIC | | | |
|---|---|---|---|---|---|---|---|---|
| | Peak Position | Peak Width | Peak Area | Peak Area Ratio | Peak Position | Peak Width | Peak Area | Peak Area Ratio |
| One Band Fit | 959.8 | 11 | 195858.8 | | 960.5 | 10.2 | 183341.1 | |
| One Band Fit | 959.5 | 7 | 42500.8 | | 960.8 | 7.7 | 64057.9 | |
| | 960 | 14.6 | 147505.8 | 3.47 | 959.8 | 16 | 113452.4 | 1.77 |

Figure 2C:
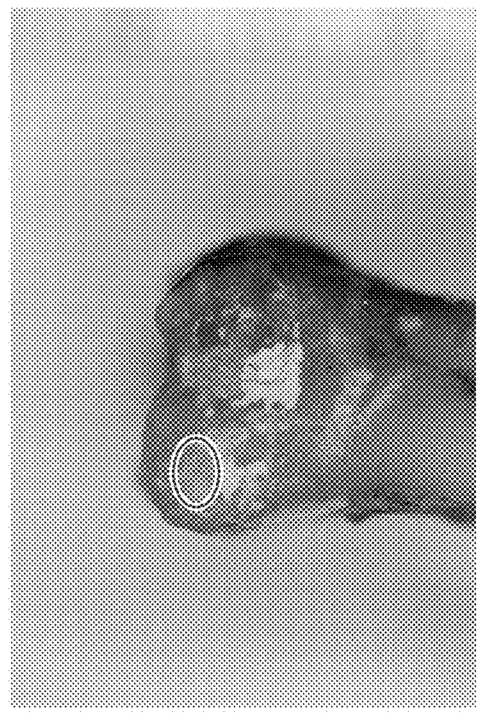
FIG. 2C shows a permanent molar used for collection of Raman spectra for MH and healthy enamel.
Figure 2B:
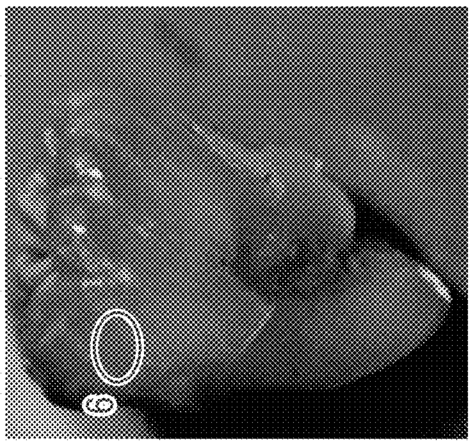
FIG. 2A and FIG. 2B are two different views of the same permanent molar showing differences in the Raman spectroscopy signature from regions of healthy enamel and defective enamel.
Figure 2A:
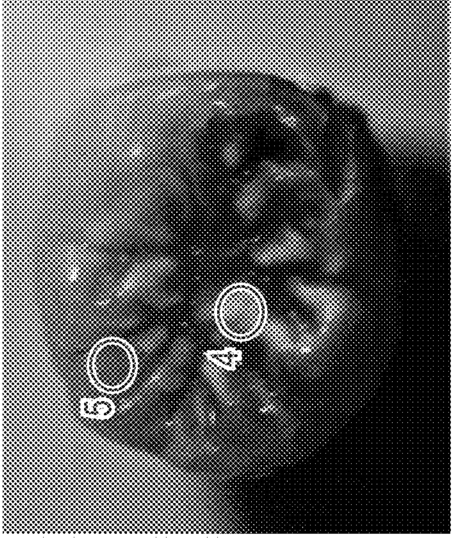

FIG. 2A is top view of a human permanent molar and FIG. 2B is a side view of the same molar. A visual scan of the tooth shows an area of suspected enamel hypomineralization (4), areas of healthy enamel (5), and an area having a thin layer of enamel after grinding (6).

Raman spectra for MH and fluorosis differ in the literature: Raman results from independent studies on MH and fluorosis present different spectral profiles for both conditions. The differences are sufficiently large to discriminate one condition from the other.

Figure 3:
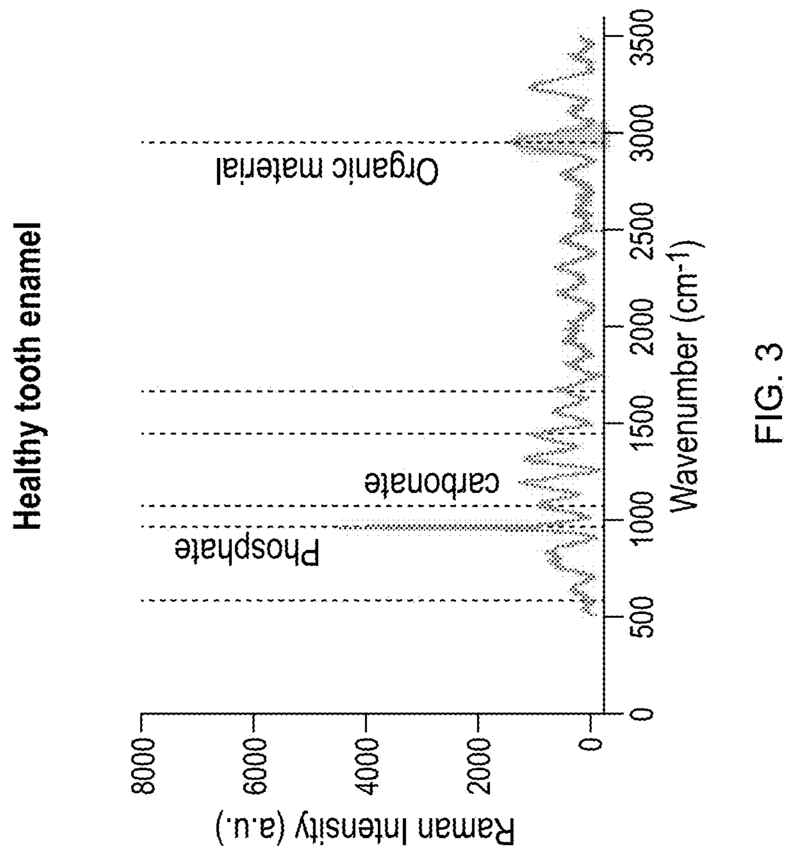
FIG. 3 illustrates an example of a Raman spectrum of healthy tooth enamel.

FIG. 3 illustrates the Raman spectra analysis of healthy tooth enamel.

Figure 4:
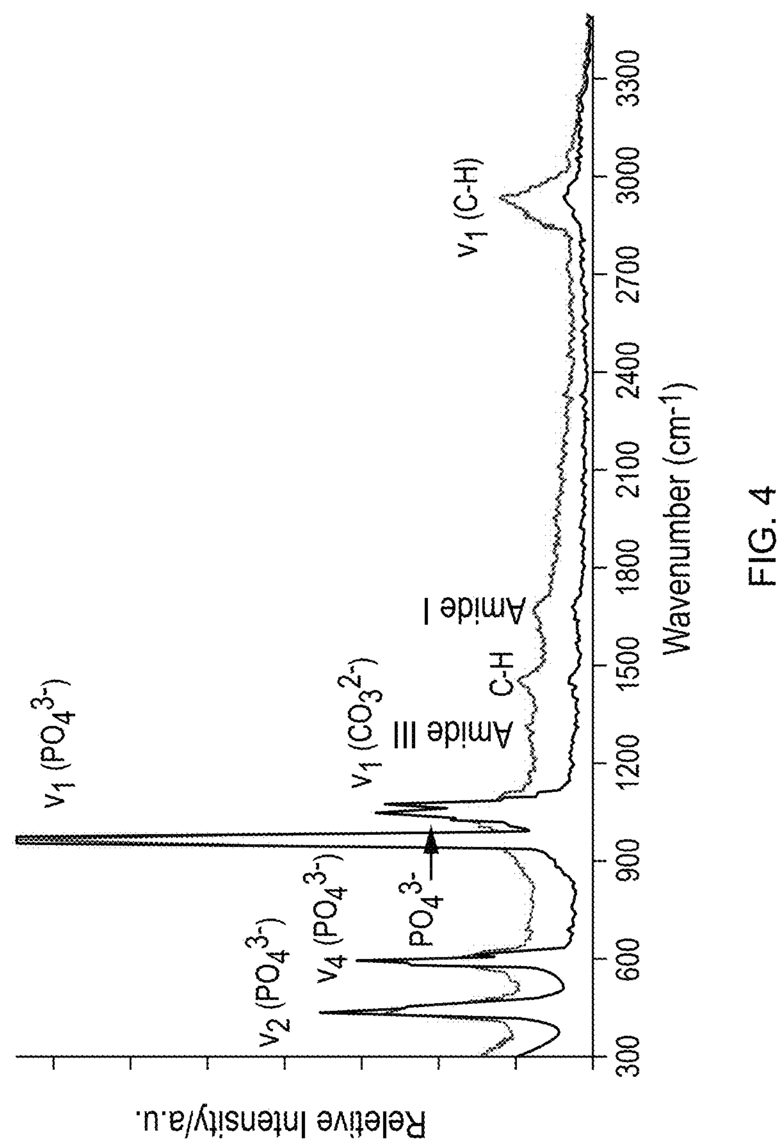
FIG. 4 illustrates the spectral profile of enamel affected by fluorosis.

FIG. 4 illustrates the spectral profile of enamel affected by fluorosis from "Deviations of inorganic and organic carbon content in hypomineralised enamel," by Taube et al., Journal of Dentistry (2015). Raman spectra of molar incisor hypomineralization (MIH) affected enamel with hypomineralized enamel shown in red line, compared to healthy, normal enamel (black line). In MIH samples, bands at 2925-2937 cmS1 and 1465 cmS1, arising from hydrocarbons, has a significant increased area, as well as bands arising from amide I, i.e. 1673 cmS1, and the carbonate band at 1071 cmS1, arising from B-type carbonate.

Figure 5:
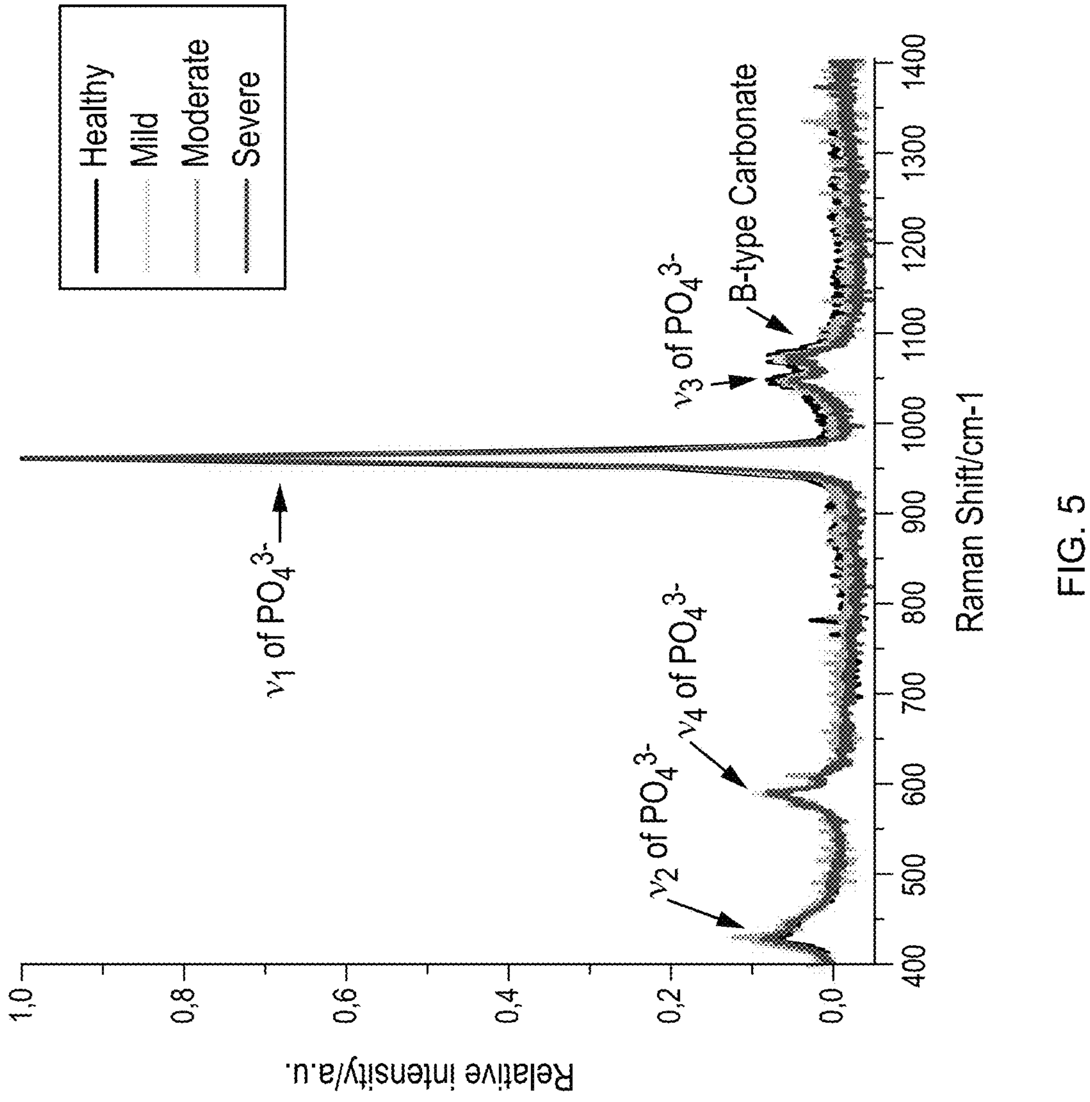
FIG. 5 illustrates the spectral profile of MH affected enamel from FIG. 2A.

FIG. 5 illustrates the spectral profile of MH affected enamel. from "Analysis of the molecular structure of human enamel with fluorosis using micro-Raman spectroscopy," by Zavala-Alonso et al, Journal of Oral Science (2012). Micro-Raman Spectra of tooth enamel with different degrees of fluorosis compared to health y enamel, showing that severe fluorosis has less carbonate substitutions in the hydroxyapatite of fluorotic enamel.

Figure 6:
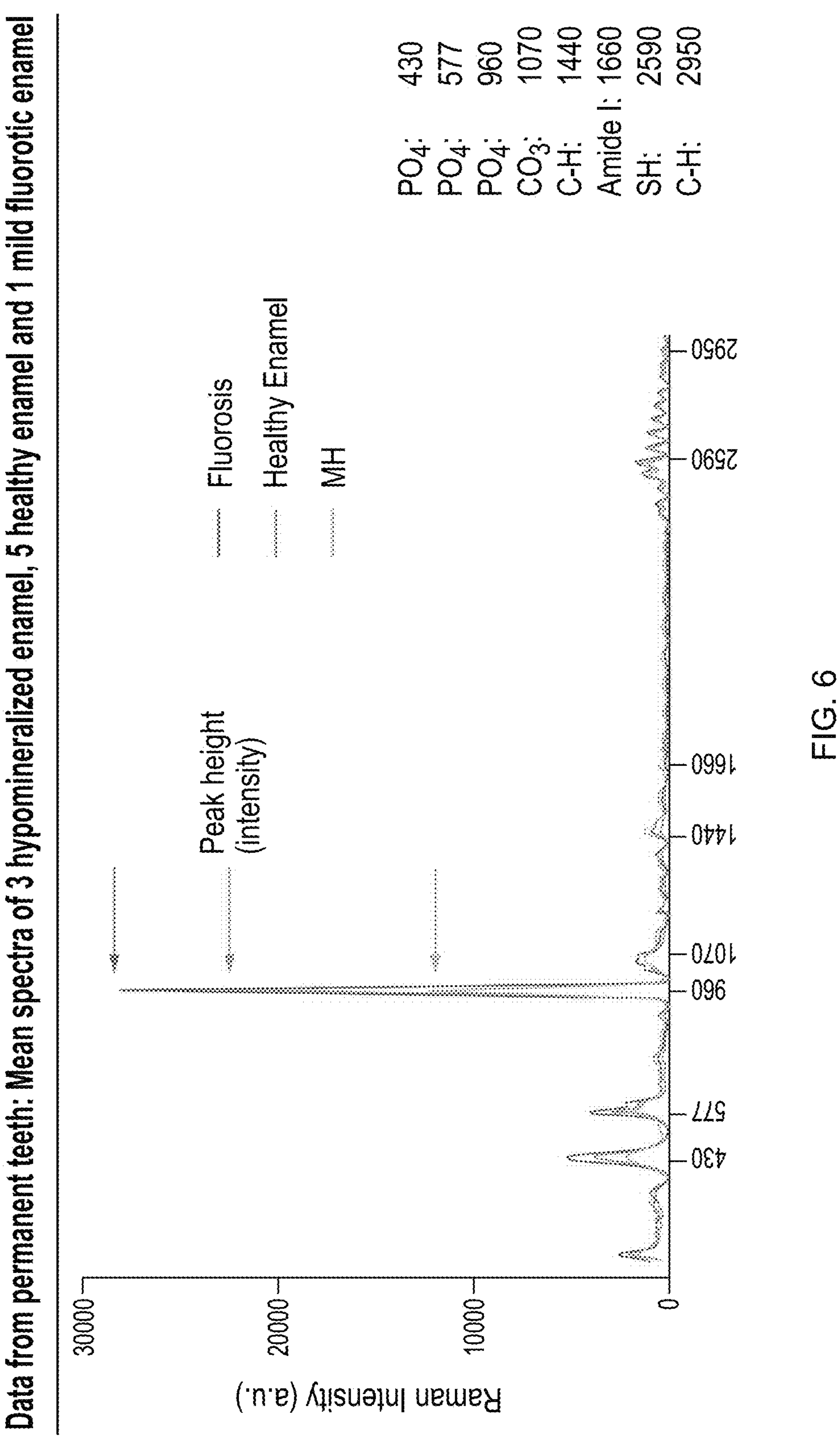
FIG. 6 is the mean Raman spectral of 3 hypomineralized enamel, 5 healthy enamel and 1 mild fluorotic enamel.

FIG. 6 is the mean Raman spectra of 3 hypomineralized enamel, 5 healthy enamel and 1 mild fluorotic enamel.

According to some aspects, the systems described herein create an evaluation profile of the target surface by evaluating the Raman intensity values associated with inorganic components of PO4 with peak positions at 430 cm-1, 577 cm-1, 960 cm-1, and CO3 at 1070 cm-1, and organic components C—H at 1440 cm-1, SH at 2590 cm-1 and C—H at 2950 cm-11.0. Using the evaluation profile, the system identifies hypomineralization and a type of enamel defect through proximity of the evaluation profile to a fingerprint of hypomineralization profile characterized by PO4 (430 cm-1), PO4 (577 cm-1), PO4 (960 cm-1), and CO3 (1070 cm-1), C—H (1440 cm-1), SH (2590 cm-1) and C—H (2950 cm-1). If hypomineralization is identified, notice is provided to a user. In some embodiments, the system may provide the user with the type of enamel defect identified.

A statistically significant difference between these regions is detected in the properties of mineral (abundance, crystallinity, phase) and the properties of the organic content of enamel (abundance and composition). These findings as described further below in reference to FIGS. 7-13 confirm that Raman spectra collected on teeth not only are providing a specific spectral fingerprint, but can be used to reliably discern between the enamel defects of fluorosis and MH in primary and permanent teeth. Other methods, such as OCT alone, can detect the lower mineral content, but cannot distinguish between these two enamel defects. The use of Raman analyses provides a novel method for accurately diagnosing in vivo MH that significantly reduces the rate of misdiagnosing the condition as fluorosis.

Figure 7:
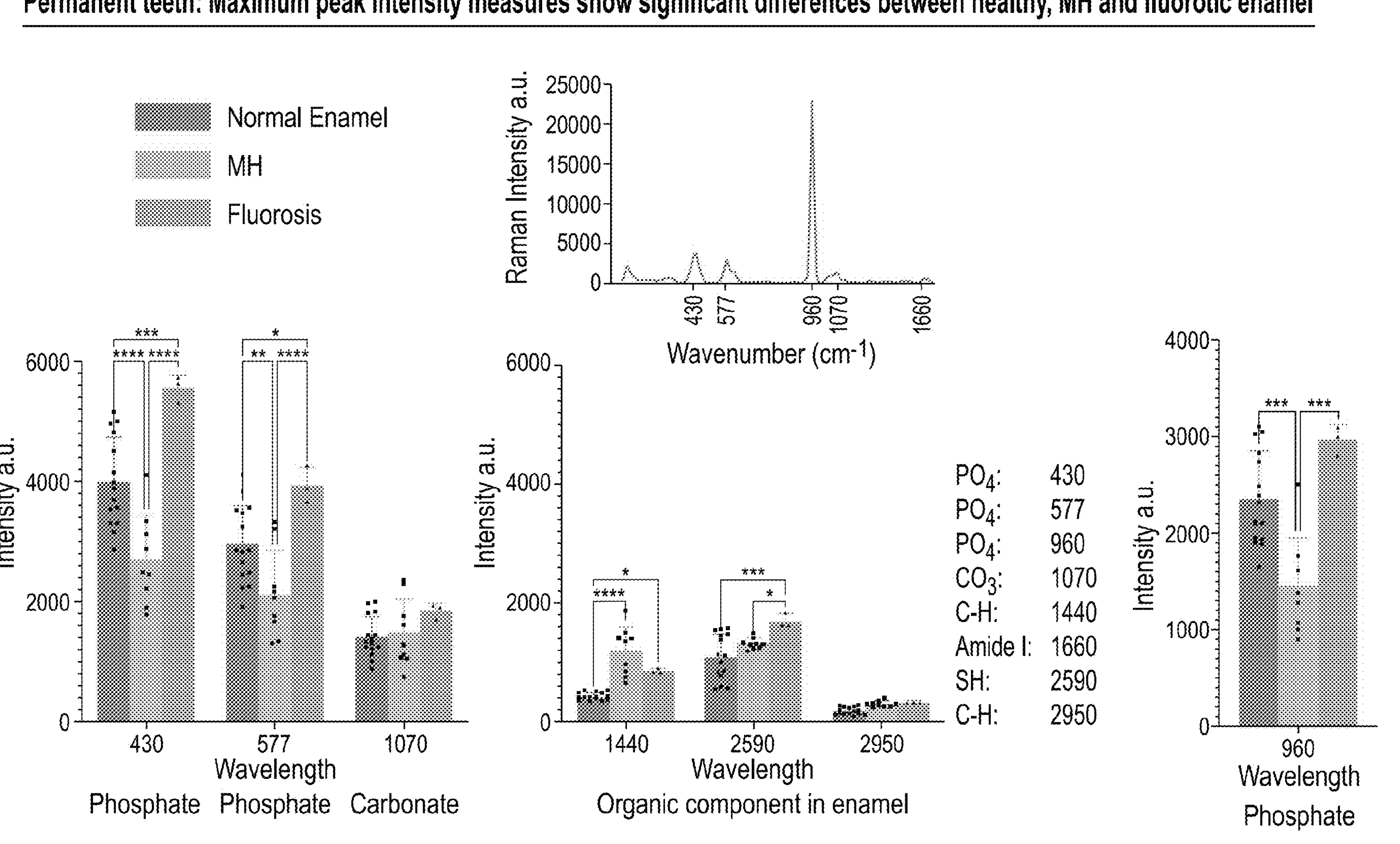
FIG. 7 illustrates sample maximum peak intensity Raman spectral analysis measurements on areas of permanent teeth having healthy enamel, fluorosis and MH.
Figure 8:
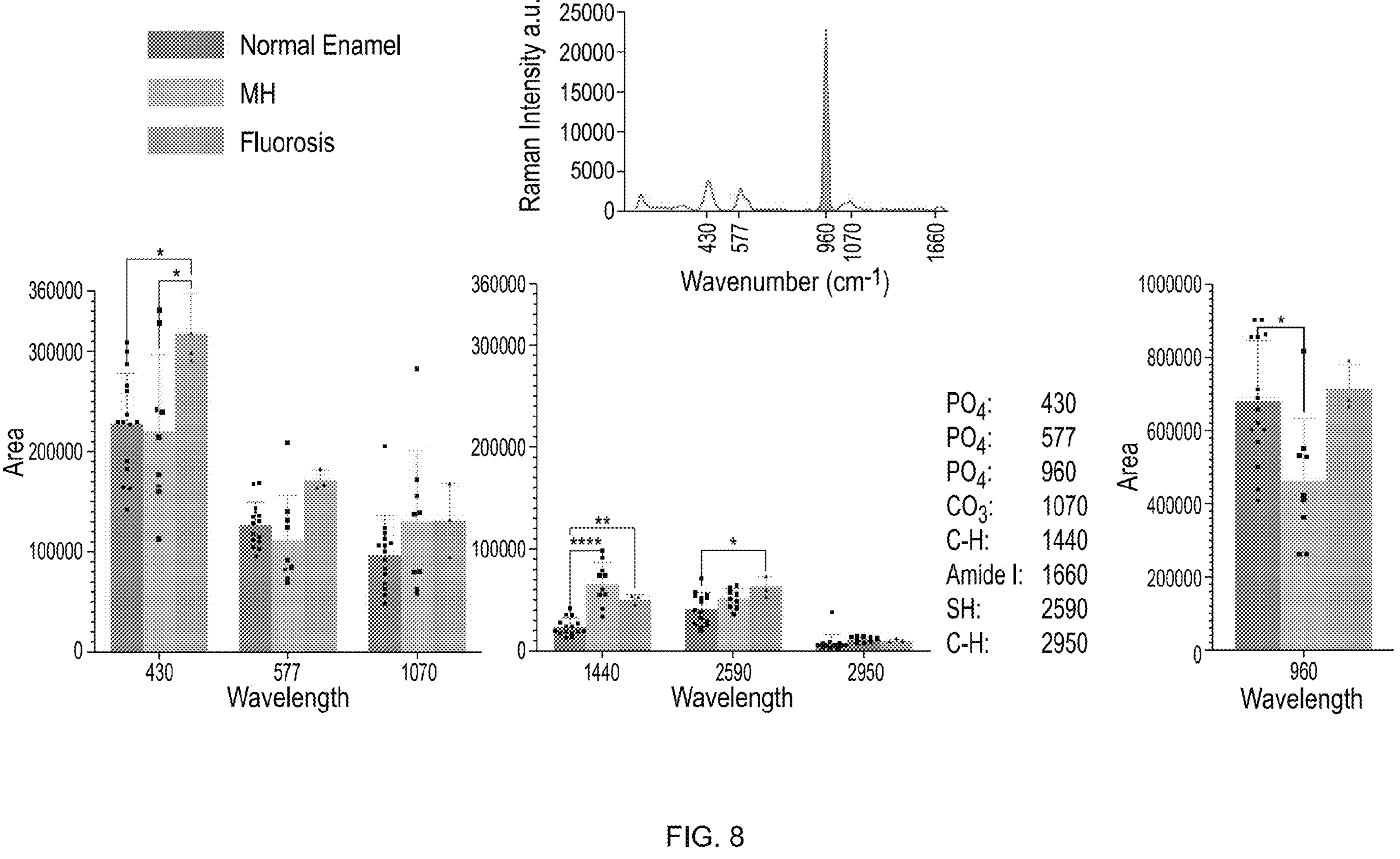
FIG. 8 illustrates sample measures under the curve of Raman spectral analysis measurements on areas of permanent teeth having healthy enamel, fluorosis and MH.
Figure 9:
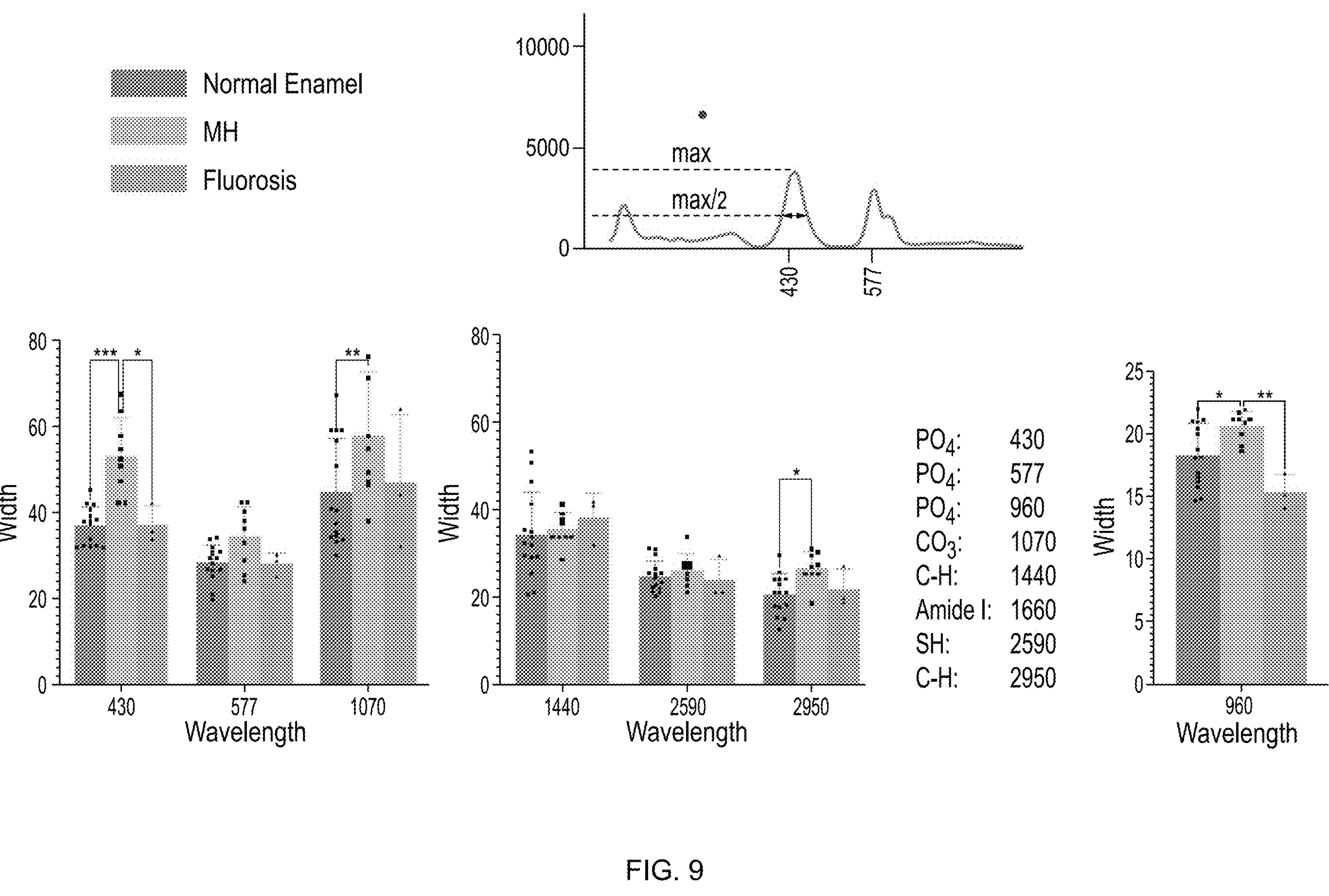
FIG. 9 illustrates sample full width at half maximum data of Raman spectral analysis measurements on areas of permanent teeth having healthy enamel, fluorosis and MH.

FIGS. 7, 8, and 9 illustrate various spectral analysis measures on permanent teeth. FIG. 7 illustrates sample maximum peak intensity Raman spectral analysis measurements on areas of permanent teeth having healthy enamel, fluorosis and MH. Maximum peak intensity measures show significant differences between healthy, MH and fluorotic enamel. FIG. 8 illustrates sample measures under the curve of Raman spectral analysis measurements on areas of permanent teeth having healthy enamel, fluorosis and MH. The area under the curve is a measure of the accuracy of a quantitative diagnostic test. From FIG. 8, the measures of the area under the curve also shows significant differences between healthy, MH, and fluorotic enamel. FIG. 9 illustrates sample full width at half maximum data of Raman spectral analysis measurements on areas of permanent teeth having healthy enamel, fluorosis and MH. Measures of the full width at half maximum data also shows significant differences at phosphate, carbonate, and protein peaks.

Figure 10:
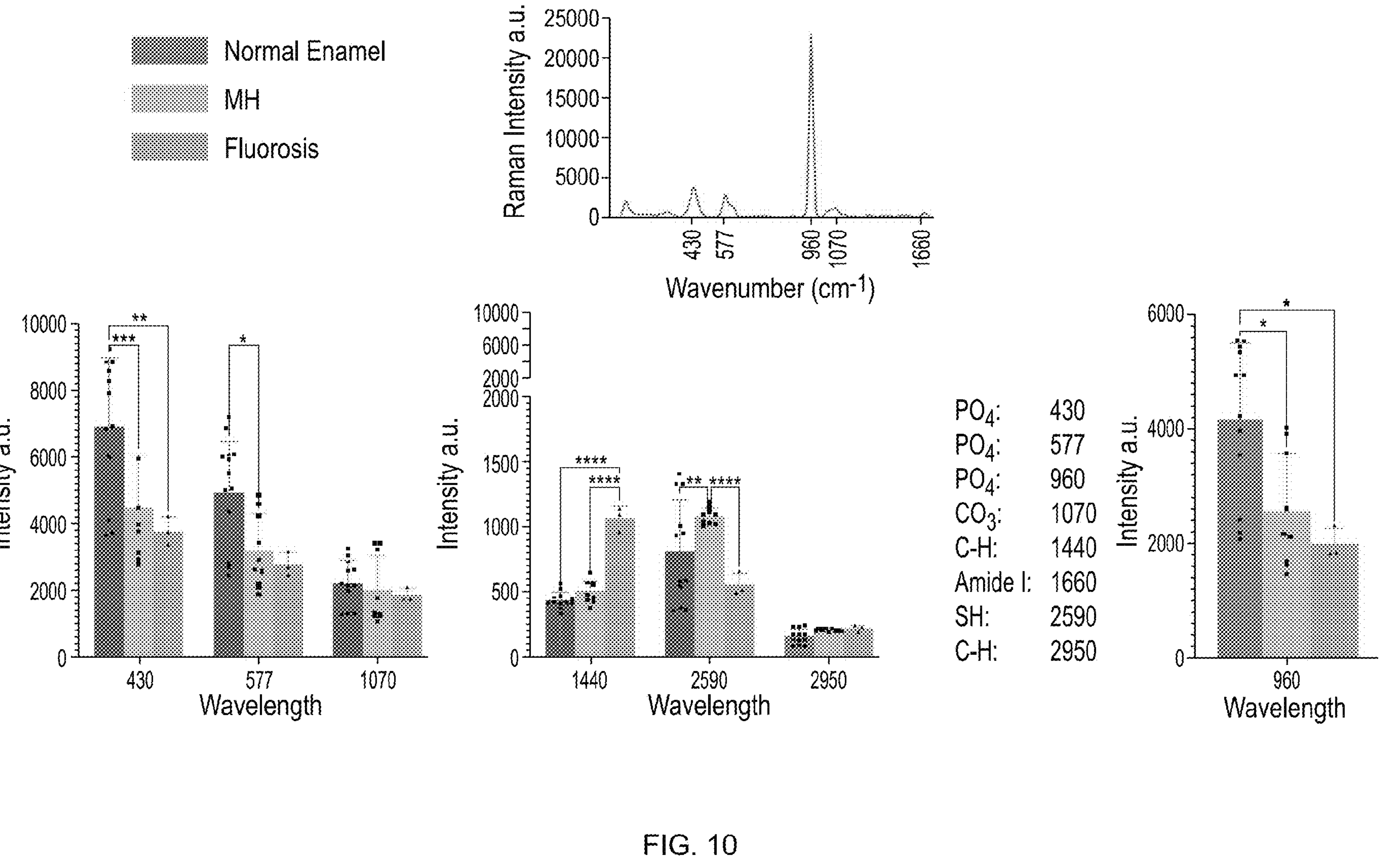
FIG. 10 illustrates sample maximum peak intensity Raman spectral analysis measurements on areas of primary teeth having healthy enamel, fluorosis and MH.
Figure 11:
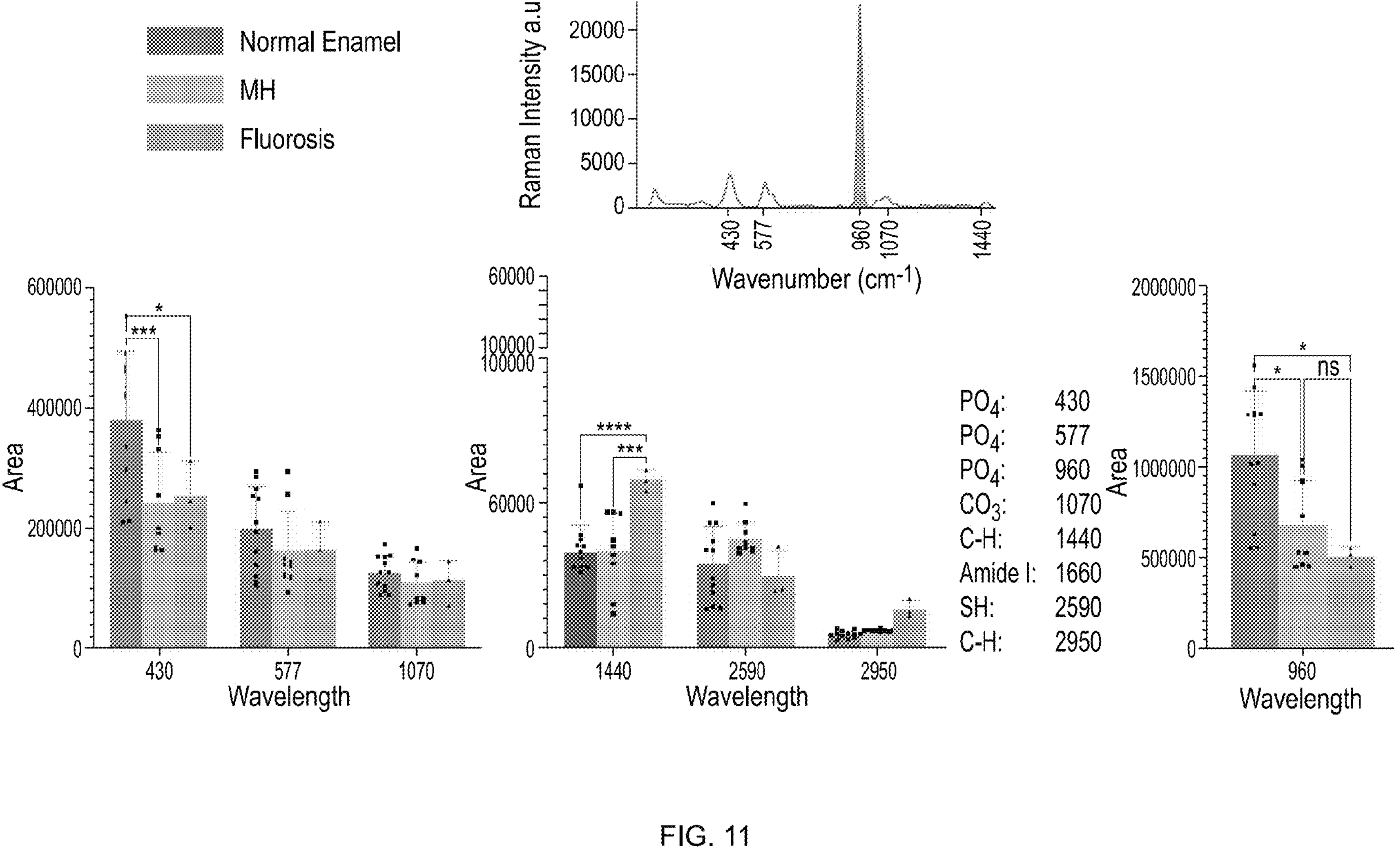
FIG. 11 illustrates sample measures under the curve of Raman spectral analysis measurements on areas of primary teeth having healthy enamel, fluorosis and MH.
Figure 12:
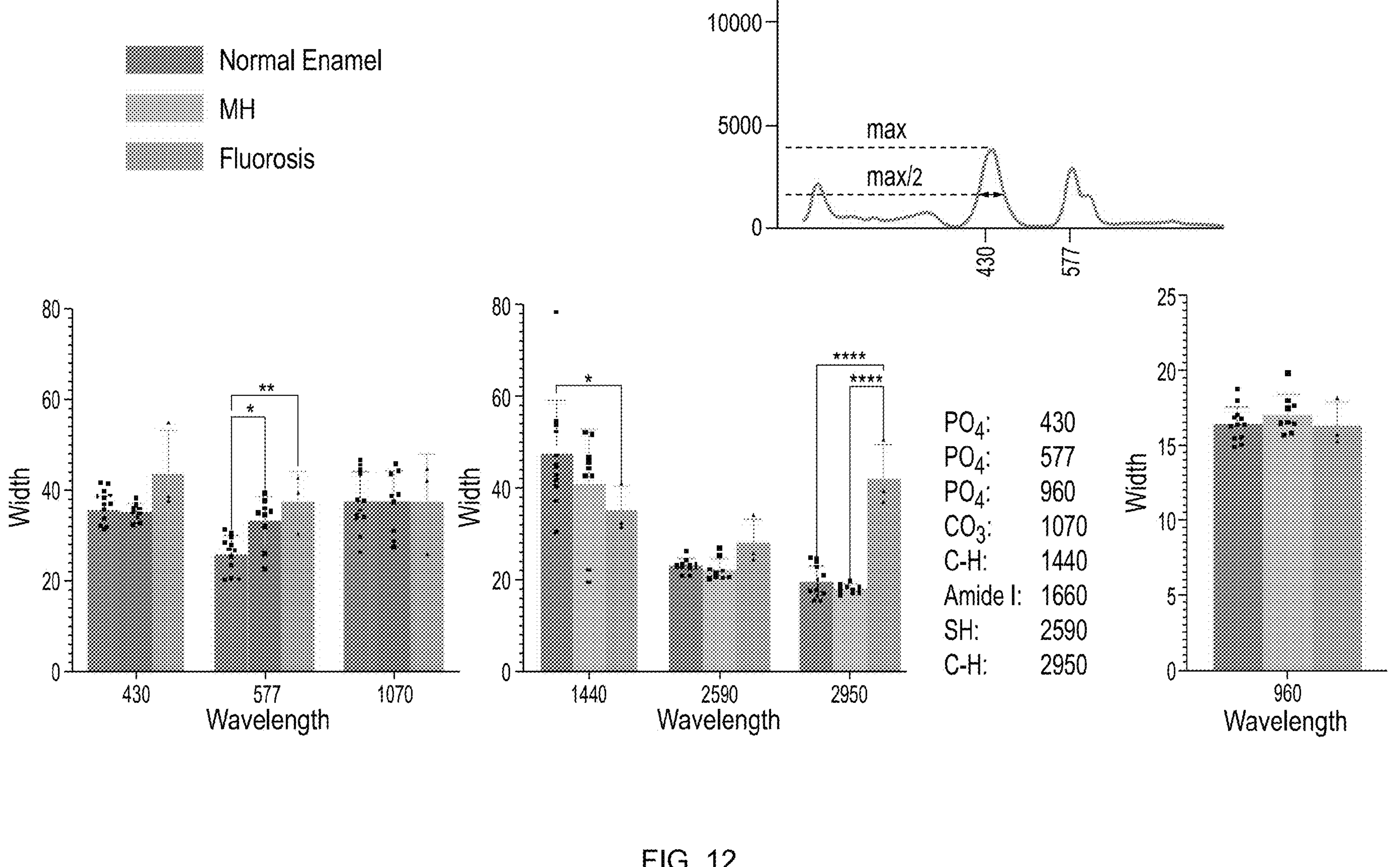
FIG. 12 illustrates sample full width at half maximum data of Raman spectral analysis measurements on areas of primary teeth having healthy enamel, fluorosis and MH.

FIGS. 10, 11, and 12 illustrate various spectral analysis measures on primary teeth. FIG. 10 illustrates sample maximum peak intensity Raman spectral analysis measurements on areas of primary teeth having healthy enamel, fluorosis and MH. Maximum peak intensity measures show significant differences between healthy, MH and fluorotic enamel. FIG. 11 illustrates sample measures under the curve of Raman spectral analysis measurements on areas of primary teeth having healthy enamel, fluorosis and MH. The area under the curve significantly differs for phosphate and protein peaks between health, MH and fluorotic enamel. FIG. 12 illustrates sample full width at half maximum data of Raman spectral analysis measurements on areas of primary teeth having healthy enamel, fluorosis and MH. Measures of the full width at half maximum data also shows significant differences for one phosphate, and two protein peaks between health, MH and fluorotic enamel.

Using the data above, particular profiles of hypomineralization based on Raman spectra may be used as a means for identifying hypomineralization and identifying the type of enamel defect by comparing Raman spectra of enamel on the surface of a tooth in vivo.

Figure 13B:
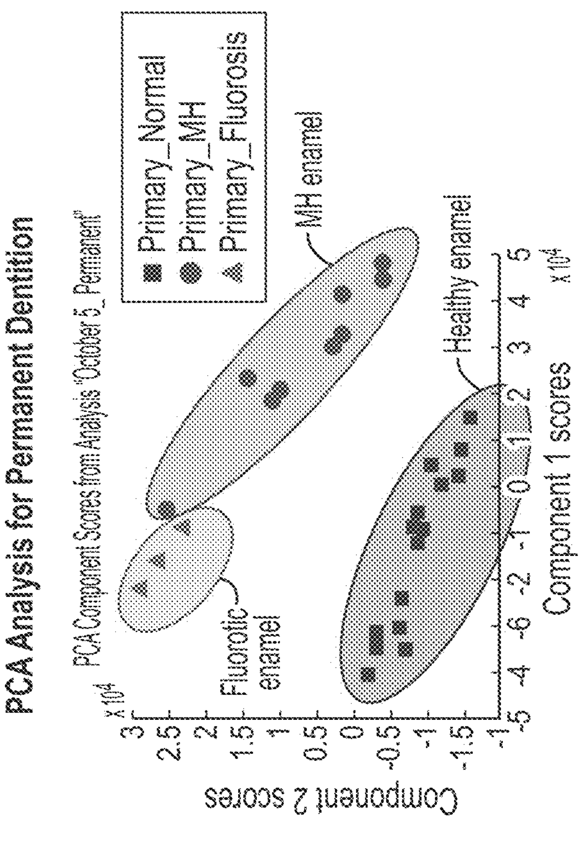
FIGS. 13A and 13B are charts showing principle component analysis of primary dentition and permanent dentition with data clustered according to defect.
Figure 13A:
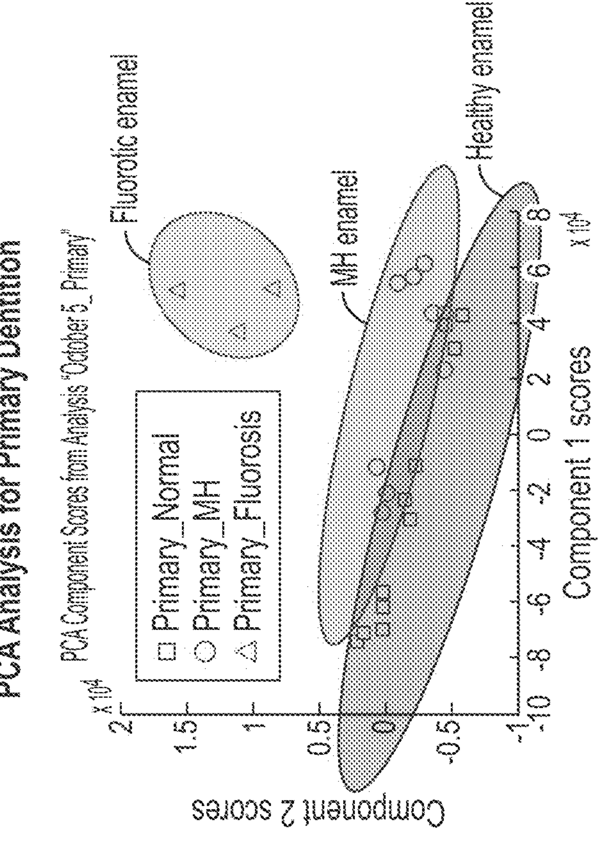

FIGS. 13A and 13 B are charts showing principle component analysis of primary dentition and permanent dentition with data clustered according to defect. A clear separation is seen between fluorotic enamel and hypomineralized enamel, that is affected by molar hypomineralization. The separation between these two clusters highlights the difference in Raman fingerprints between these two development dental defects and the usefulness of Raman fingerprints as a diagnostic tool to discern between them. These clusters may be used to calculate a composite metric that may be used to help identify and distinguish hypomineralization from fluorosis or health enamel.

Devices using Raman/optical Coherence Tomography (OCT) combined analysis, or Raman analysis alone, may be used to obtain information on chemical composition of tooth enamel from Raman data. The use in combination with OCT will provide data on mineral density that are complementary to the chemical composition data obtained by Raman analysis. The material density measurements of enamel on the surface of the tooth may include enamel thickness towards underlying dentin. This may allow for further evaluation of an extension of an enamel defect from the tooth surface through the enamel thickness towards the underlying dentin. Further, the type of hypomineralization can be further characterized by a marked increase in reflectivity to healthy enamel.

When these analyses are performed through the use of a handheld probe, it allows for applications that are different from existing suggested and targeted use. For example, it allows for the identification of tooth enamel defects both in vivo, for example in clinical settings, and ex vivo, for analyses of extracted or shed teeth, forensic or archaeological material. Specifically, it provides the ability to identify distinction between enamel fluorosis and enamel affected by the developmental defect of molar hypomineralization. By allowing in vivo readings, the analysis also aids in the diagnosis of dental developmental defects and discern between fluorosis and molar hypomineralization in tooth enamel, two enamel defects that are common and often misdiagnosed. The application of the Raman spectroscopy data for diagnostic purposes of developmental dental defects meets the need for improved diagnosis of molar hypomineralization. Further, it provides improved distinction between developmental dental defects, and improved diagnosis of fluorosis.

Figure 14:
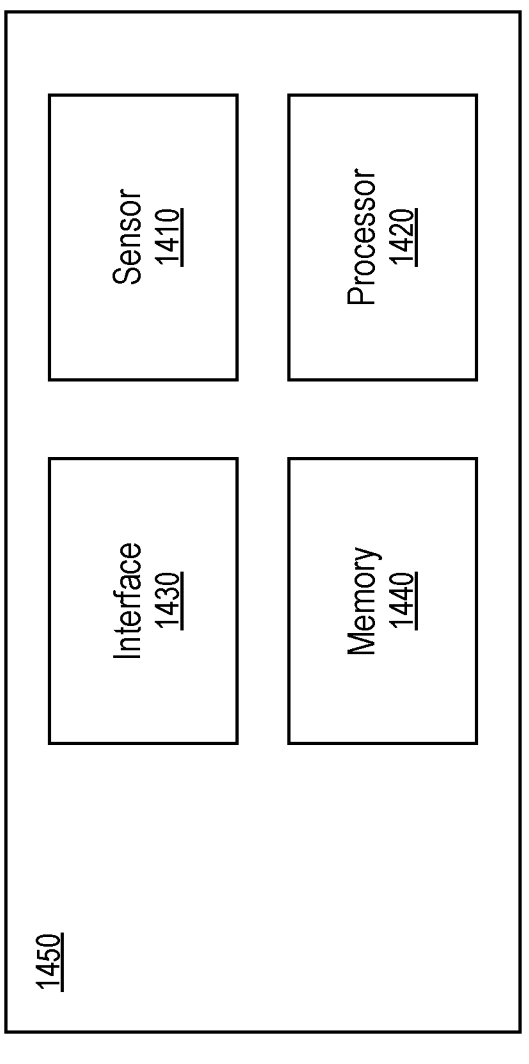
FIG. 14 is a schematic diagram of one embodiment of a system for in vivo identification of hypomineralization.

FIG. 14 is a schematic diagram of one embodiment of a system 1400 for in vivo identification of hypomineralization. The system 1400 includes a handheld device 1450 that has a sensor 1410 for obtaining Raman intensity values of chemical composition of enamel on a tooth surface. The sensor 1410 be a Raman spectrometer that includes an excitation source (e.g. laser), a sampling apparatus, and a detector (components not shown). In some embodiments, the sensor 1410 may also include an OCT device or component. The data obtained from the sensor 1410 may be used in processor 1420 to create an evaluation profile of the scanned area on the tooth surface. The evaluation profile may include the Raman intensity values associated with certain inorganic and organic components. Using the evaluation profile, the processor identifies hypomineralization and a type of enamel defect through proximity of the evaluation profile to a hypomineralization profile stored in memory 1440. The hypomineralization profile may be characterized by particular measures of peak intensity, peak broadening, and area under the curve data for the inorganic and organic components. If hypomineralization is identified, notice is provided to a user through interface 1430. In additional embodiments, the hypomineralization profiles may be updated based on data obtained from the scanned data that has been confirmed as healthy, fluorosis affected, or hypomineralized.

Figure 15:
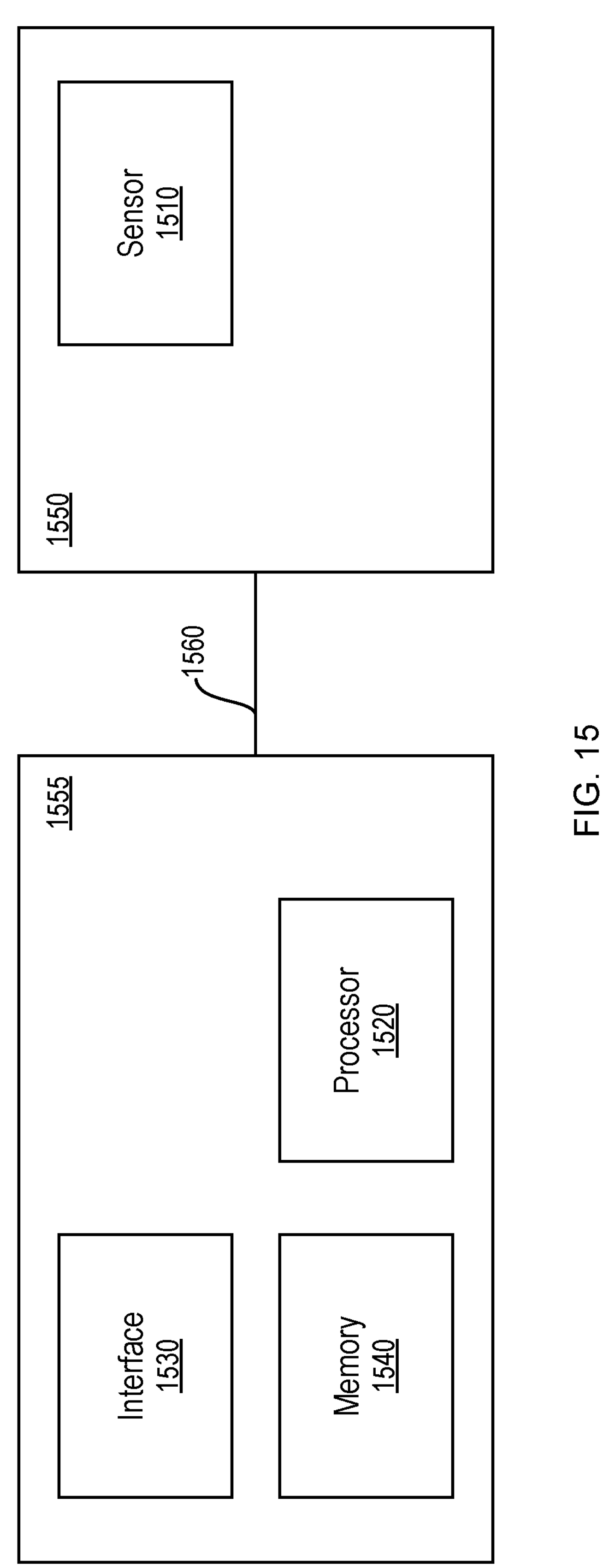
FIG. 15 is a schematic diagram of an alternative embodiment of a system for in vivo identification of hypomineralization.

FIG. 15 is a schematic diagram of an alternative embodiment of a system 1500 for in vivo identification of hypomineralization. The system 1500 includes a handheld device 1550 that has a sensor 1510, similar to the sensor 1410 described in connection with FIG. 14. The handheld device may be a standalone device connected to a computer or server 1555 that includes a processor 1520, memory 1540 and interface 1530. The handheld device 1550 may be in communication with the computer 1555 through a bus 1560. In other embodiments not shown here, the connection between the handheld device 1550 and the computer 1555 may be through any communication means, such as a local area network, a wireless area network, or through the internet.

While example embodiments have been particularly shown and described, it will be understood by those skilled in the art that various changes in form and details may be made therein without departing from the scope encompassed by the appended claims.

It should be understood that the example embodiments described above may be implemented in many different ways. In some instances, the various methods and machines described herein may each be implemented by a physical, virtual or hybrid general purpose computer having a central processor, memory, disk or other mass storage, communication interface(s), input/output (I/O) device(s), and other peripherals. The general purpose computer is transformed into the machines that execute the methods described above, for example, by loading software instructions into a data processor, and then causing execution of the instructions to carry out the functions described, herein.

As is known in the art, such a computer may contain a system bus, where a bus is a set of hardware lines used for data transfer among the components of a computer or processing system. The bus or busses are essentially shared conduit(s) that connect different elements of the computer system, e.g., processor, disk storage, memory, input/output ports, network ports, etcetera, which enables the transfer of information between the elements. One or more central processor units are attached to the system bus and provide for the execution of computer instructions. Also attached to system bus are typically I/O device interfaces for connecting various input and output devices, e.g., keyboard, mouse, displays, printers, speakers, etcetera, to the computer. Network interface(s) allow the computer to connect to various other devices attached to a network. Memory provides volatile storage for computer software instructions and data used to implement an embodiment. Disk or other mass storage provides non-volatile storage for computer software instructions and data used to implement, for example, the various procedures described herein.

Embodiments may therefore typically be implemented in hardware, firmware, software, or any combination thereof.

In certain embodiments, the procedures, devices, and processes described herein constitute a computer program product, including a non-transitory computer-readable medium, e.g., a storage medium such as one or more high-speed random access memory, such as DRAM, SRAM, DDR RAM or other random access solid state memory devices; and optionally includes non-volatile memory, such as one or more magnetic disk storage devices, optical disk storage devices, flash memory devices, or other non-volatile solid state storage devices or any combination thereof. Such a computer program product can be installed by any suitable software installation procedure, as is well known in the art. In another embodiment, at least a portion of the software instructions may also be downloaded over a cable, communication and/or wireless connection.

Further, firmware, software, routines, or instructions may be described herein as performing certain actions and/or functions of the data processors. However, it should be appreciated that such descriptions contained herein are merely for convenience and that such actions in fact result from computing devices, processors, controllers, or other devices executing the firmware, software, routines, instructions, etcetera.

It also should be understood that the flow diagrams, block diagrams, and network diagrams may include more or fewer elements, be arranged differently, or be represented differently. But it further should be understood that certain implementations may dictate the block and network diagrams and the number of block and network diagrams illustrating the execution of the embodiments be implemented in a particular way.

Accordingly, further embodiments may also be implemented in a variety of computer architectures, physical, virtual, cloud computers, and/or some combination thereof, and, thus, the data processors described herein are intended for purposes of illustration only and not as a limitation of the embodiments.

While this invention has been particularly shown and described with references to example embodiments thereof, it will be understood by those skilled in the art that various changes in form and details may be made therein without departing from the scope of the invention encompassed by the appended claims.

What is claimed is:

1. A method for in vivo identification of hypomineralization and distinction between enamel defects, the method executed by a processor and comprising:

obtaining, in memory coupled to the processor, measurements of chemical composition and mineral properties of enamel on a target surface of a tooth in vivo from a Raman spectroscope;

creating an evaluation profile of the target surface by evaluating Raman spectra including derived measures for the obtained chemical composition measurements in the memory, the derived measures including at least one of peak positions, peak width, intensity values, and area under curve, and the evaluation profile being associated with at least one inorganic component selected from the group consisting of inorganic components $PO4^{3-}$ and $CO3^{2-}$ and the evaluation profile being further associated with at least one organic component selected from the group consisting of organic components C—H and SH;

calculating a composite metric of the evaluation profile based on measures derived from the Raman spectra associated with the at least one inorganic component and the at least one organic component of the evaluation profile;

identifying hypomineralization and discerning a type of enamel defect through proximity of the composite metric of the evaluation profile to a composite metric associated with known hypomineralization, the discerning the type of enamel defect through the proximity of the composite metric of the evaluation profile to the composite metric associated with known hypomineralization including distinguishing between fluorosis and molar hypomineralization, as characterized by demarcated opacity, wherein the molar hypomineralization comprises at least one of molar incisor hypomineralization, deciduous molar hypomineralization, hypomineralized primary incisors, hypomineralized first primary molars, hypomineralized second primary molars, hypomineralized permanent incisors, and hypomineralized permanent molars; and responsive to identifying hypomineralization, providing notice to a user, via an interface on a display coupled to the processor.

2. The method of claim 1 further comprising providing notice to the user of the type of enamel defect discerned.

3. The method of claim 1 further comprising:

obtaining material density measurements of enamel on the target surface of the tooth, including enamel thickness towards underlying dentin, wherein creating the evaluation profile further includes evaluating an extension of an enamel defect from the target surface of the tooth through the enamel thickness towards the underlying dentin; and determining an indication of differences in type of hypomineralization characterized by a marked increase in reflectivity to healthy enamel.

4. The method of claim 3 wherein the material density is obtained through data collection with a handheld optical coherence tomography (OCT) device.

5. The method of claim 3 wherein the material density and the chemical composition measurements are obtained with a non-invasive fiber optic sensor.

6. The method of claim 1 further including:

obtaining an image of the tooth;

generating an adjusted image of the tooth highlighting an intensity value of the composite metric of the evaluation profile obtained at a particular portion of the tooth; and displaying the adjusted image highlighting the intensity value of the composite metric.

7. A system for in vivo identification of hypomineralization comprising:

a handheld device configured to obtain measurements of chemical composition and mineral properties of enamel on a surface of a tooth in vivo and store the obtained measurements in memory, wherein the obtained measurements are associated with at least one inorganic component selected from the group consisting of inorganic components $PO4^{3-}$ and $CO3^{2-}$, and wherein the obtained measurements are further associated with at least one organic component selected from the group consisting of organic components C—H and SH;

a processor, coupled to the memory and configured to i) create an evaluation profile by evaluating the Raman spectra including derived measures for the obtained chemical composition measurements in the memory, the derived measures including at least one of peak positions, peak width, intensity values, and area under curve, and the evaluation profile being associated with the at least one inorganic component and with the at least one organic component;

ii) calculate a composite metric of the evaluation profile based on measures derived from the Raman spectra associated with the at least one inorganic component and the at least one organic component of the evaluation profile;

iii) identify hypomineralization and discern a type of enamel defect through proximity of the composite metric of the evaluation profile to a composite metric associated with known hypomineralization; and (iv) based on the proximity of the composite metric of the evaluation profile to the composite metric associated with known hypomineralization, distinguish between fluorosis and molar hypomineralization, as characterized by demarcated opacity, wherein the molar hypomineralization comprises at least one of molar incisor hypomineralization, deciduous molar hypomineralization, hypomineralized primary incisors, hypomineralized first primary molars, hypomineralized second primary molars, hypomineralized permanent incisors, and hypomineralized permanent molars; and a display coupled to the processor and configured, responsive to identifying hypomineralization, to provide, via an interface on the display, notice to a user.

8. The system of claim 7 wherein the interface is further configured to provide notice to the user of the type of enamel defect discerned.

9. The system of claim 7 wherein:

the handheld device is further configured to obtain material density measurements of enamel on the surface of the tooth, including enamel thickness towards underlying dentin, wherein the processor further evaluates an extension of an enamel defect from the surface of the tooth through the enamel thickness towards the underlying dentin; and the processor further determines an indication of differences in type of hypomineralization characterized by a marked increase in reflectivity to healthy enamel.

10. The system of claim 9 wherein the handheld device includes an optical coherence tomography (OCT) device.

11. The system of claim 9 wherein the handheld device includes a non-invasive fiber optic sensor.

12. The system of claim 7 further including:

an image acquisition device configured to obtain an image of the tooth; and wherein the processor is further configured to generate an adjusted image of the tooth highlighting an intensity value of the composite metric of the evaluation profile obtained at a particular portion of the tooth, and display the adjusted image on the display.

* * * * *